(12) United States Patent
Nowakowski (10) Patent No.: US 10,973,503 B2
(45) Date of Patent: *Apr. 13, 2021

(54) FAILSAFE PERCUTANEOUS WOUND BARRIER

(71) Applicant: ST. CROIX SURGICAL SYSTEMS, LLC, Circle Pines, MN (US)

(72) Inventor: Karol Leon Nowakowski, Circle Pines, MN (US)

(73) Assignee: ST. CROIX SURGICAL SYSTEMS, LLC, Lakeland, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,354

(22) Filed: Jan. 29, 2019

(65) Prior Publication Data

US 2019/0388075 A1    Dec. 26, 2019

Related U.S. Application Data

(63) Continuation of application No. 14/756,544, filed on Sep. 16, 2015, now Pat. No. 10,231,721, which is a
(Continued)

(51) Int. Cl.
*A61B 17/00* (2006.01)

(52) U.S. Cl.
CPC .... *A61B 17/0057* (2013.01); *A61B 17/00491* (2013.01); *A61B 2017/00654* (2013.01)

(58) Field of Classification Search
CPC .......... A61B 17/00491; A61B 17/0057; A61B 2017/00654; A61B 2017/00884
See application file for complete search history.

(56) References Cited

U.S. PATENT DOCUMENTS

| 3,223,083 A | 12/1965 | Cobey |
| 3,956,480 A | 5/1976 | Dichter et al. |

(Continued)

FOREIGN PATENT DOCUMENTS

| CA | 2008114 | 7/1990 |
| EP | 0466178 | 1/1992 |

(Continued)

OTHER PUBLICATIONS

Orlikowski, Effect of Delay and Storage on Whole-Blood Clotting Analysis as Determined by Thrombelastography, Journal of Clinical Monitoring, 1993, vol. 9, pp. 5-8. Reference submitted in U.S. Appl. No. 14/756,544.

(Continued)

*Primary Examiner* — Melanie R Tyson
(74) *Attorney, Agent, or Firm* — Gardella Grace P.A.

(57) ABSTRACT

Provided are approaches to establish a failsafe barrier to internal bleeding from percutaneous wounds to protect a patient from failed wound closure devices or related complications due to a variety of contributing factors such as state of systemic anticoagulation, errors in surgical procedure, variability in patient anatomy, and the like. Systems include a clotting agent to encase, and thus isolate, substantially the entire wound access area from the rest of the patient and an instrument, such as an intravascular introducer sheath, inserted through a wound at an access site on a vessel, for delivering the clotting agent to the entire enveloping tissue region around the accessed area as a mold cavity to be filled with the clotting agent. With benefits of patient safety, user simplicity, and low healthcare cost driving the effort, autologous whole blood is the preferred injected agent.

20 Claims, 7 Drawing Sheets

Related U.S. Application Data continuation-in-part of application No. 13/162,655, filed on Jun. 17, 2011, now abandoned.

(60) Provisional application No. 61/398,389, filed on Jun. 24, 2010, provisional application No. 61/404,358, filed on Oct. 1, 2010, provisional application No. 61/404,935, filed on Oct. 12, 2010.

(56) References Cited

U.S. PATENT DOCUMENTS

| | | |
|---|---|---|
| 4,048,064 A | 9/1977 | Clark, III |
| 4,265,233 A | 5/1981 | Sugitachi et al. |
| 4,277,463 A | 7/1981 | Tomic |
| 4,304,766 A | 12/1981 | Chang |
| 4,347,243 A | 8/1982 | Schneider |
| 4,359,049 A | 11/1982 | Redl et al. |
| 4,361,552 A | 11/1982 | Baur, Jr. |
| 4,373,023 A | 2/1983 | Langer et al. |
| 4,381,776 A | 5/1983 | Latham, Jr. |
| 4,531,943 A | 7/1985 | Van Tassel et al. |
| 4,532,043 A | 7/1985 | Prud'homme et al. |
| 4,565,740 A | 1/1986 | Golander et al. |
| 4,738,658 A | 4/1988 | Magro et al. |
| 4,744,364 A | 5/1988 | Kensey |
| 4,838,280 A | 6/1989 | Haaga |
| 4,852,568 A | 8/1989 | Kensey |
| 4,890,612 A | 1/1990 | Kensey |
| 4,935,204 A | 6/1990 | Seidel et al. |
| 5,000,854 A | 3/1991 | Yang |
| 5,021,059 A | 6/1991 | Kensey et al. |
| 5,030,215 A | 7/1991 | Morse et al. |
| 5,041,129 A | 8/1991 | Hayhurst et al. |
| 5,129,882 A | 7/1992 | Weldon et al. |
| 5,151,192 A | 9/1992 | Matkovich et al. |
| 5,165,938 A | 11/1992 | Knighton |
| 5,192,300 A | 3/1993 | Fowler |
| 5,197,971 A | 3/1993 | Bonutti |
| 5,209,776 A | 5/1993 | Bass et al. |
| 5,221,259 A | 6/1993 | Weldon et al. |
| 5,222,974 A | 6/1993 | Kensey et al. |
| 5,226,877 A | 7/1993 | Epstein |
| 5,275,616 A | 1/1994 | Fowler |
| 5,281,197 A | 1/1994 | Arias et al. |
| 5,290,310 A | 3/1994 | Makower et al. |
| 5,292,332 A | 3/1994 | Lee |
| 5,310,407 A | 5/1994 | Casale |
| 5,318,524 A | 6/1994 | Morse et al. |
| 5,324,306 A | 6/1994 | Makower et al. |
| 5,383,896 A | 1/1995 | Gershony et al. |
| 5,405,607 A | 4/1995 | Epstein |
| 5,413,571 A | 5/1995 | Katsaros et al. |
| 5,419,765 A | 5/1995 | Weldon et al. |
| 5,437,292 A | 8/1995 | Kipshidze et al. |
| 5,443,481 A | 8/1995 | Lee |
| 5,447,502 A | 9/1995 | Haaga |
| 5,486,195 A | 1/1996 | Myers et al. |
| 5,496,332 A | 3/1996 | Sierra et al. |
| 5,510,102 A | 4/1996 | Cochrum |
| 5,529,577 A | 6/1996 | Hammerslag |
| 5,532,311 A | 7/1996 | Sirvio et al. |
| 5,571,181 A | 11/1996 | Li |
| 5,585,007 A | 12/1996 | Antanavich et al. |
| 5,591,205 A | 1/1997 | Fowler |
| 5,601,602 A | 2/1997 | Fowler |
| 5,624,669 A | 4/1997 | Leung et al. |
| 5,648,070 A | 7/1997 | Brian, III et al. |
| 5,648,265 A | 7/1997 | Epstein |
| 5,674,394 A | 10/1997 | Whitmore |
| 5,676,689 A | 10/1997 | Kensey et al. |
| 5,700,559 A | 12/1997 | Sheu et al. |
| 5,716,375 A | 2/1998 | Fowler |
| 5,725,551 A | 3/1998 | Myers et al. |
| 5,739,288 A | 4/1998 | Edwardson et al. |
| 5,741,223 A | 4/1998 | Janzen et al. |
| 5,741,283 A | 4/1998 | Fahy |
| 5,750,657 A | 5/1998 | Edwardson et al. |
| 5,763,410 A | 6/1998 | Edwardson et al. |
| 5,763,411 A | 6/1998 | Edwardson et al. |
| 5,766,206 A | 6/1998 | Wijkamp et al. |
| 5,770,194 A | 6/1998 | Edwardson et al. |
| 5,782,860 A | 7/1998 | Epstein et al. |
| 5,788,662 A | 8/1998 | Antanavich et al. |
| 5,795,571 A | 8/1998 | Cederholm-Williams et al. |
| 5,810,810 A | 9/1998 | Tay et al. |
| 5,814,066 A | 9/1998 | Spotnitz |
| 5,830,130 A | 11/1998 | Janzen et al. |
| 5,843,124 A | 12/1998 | Hammerslag |
| 5,885,647 A | 3/1999 | Larm et al. |
| 5,916,236 A | 6/1999 | Van de Moer et al. |
| 5,948,425 A | 9/1999 | Janzen et al. |
| 5,957,952 A | 9/1999 | Gershony et al. |
| 5,962,026 A | 10/1999 | Edwardson et al. |
| 5,964,782 A | 10/1999 | Lafontaine et al. |
| 5,968,090 A | 10/1999 | Ratcliff et al. |
| 5,980,972 A | 11/1999 | Ding |
| 6,007,563 A | 12/1999 | Nash et al. |
| 6,033,427 A | 3/2000 | Lee |
| 6,077,507 A | 6/2000 | Edwardson et al. |
| 6,096,798 A | 8/2000 | Luthra et al. |
| 6,110,721 A | 8/2000 | Gibbs et al. |
| 6,127,448 A | 10/2000 | Domb |
| 6,146,771 A | 11/2000 | Wirt et al. |
| 6,159,232 A | 12/2000 | Nowakowski |
| 6,197,289 B1 | 3/2001 | Wirt et al. |
| 6,200,532 B1 | 3/2001 | Wu et al. |
| 6,340,465 B1 | 1/2002 | Hsu et al. |
| 6,451,871 B1 | 9/2002 | Winterton et al. |
| 6,482,223 B1 | 11/2002 | Nowakowski et al. |
| 6,605,294 B2 | 8/2003 | Sawhney |
| 6,733,471 B1 | 5/2004 | Ericson et al. |
| 6,887,974 B2 | 5/2005 | Pathak |
| 6,896,926 B2 | 5/2005 | Qiu et al. |
| 6,926,965 B2 | 8/2005 | Qiu et al. |
| 6,940,580 B2 | 9/2005 | Winterton et al. |
| 6,955,682 B2 | 10/2005 | Luthra et al. |
| 6,989,022 B2 | 1/2006 | Nowakowski |
| 7,008,442 B2 | 3/2006 | Brightbill |
| 7,297,725 B2 | 11/2007 | Winterton et al. |
| 7,316,845 B2 | 1/2008 | Hubbell et al. |
| 7,727,251 B2 | 6/2010 | Spurchise et al. |
| 7,771,454 B2 | 8/2010 | Michlitsch |
| 10,231,721 B2 * | 3/2019 | Nowakowski, Sr. .................. A61B 17/0057 |
| 2001/0001316 A1 * | 5/2001 | Nowakowski ...... A61L 24/0005 606/214 |
| 2005/0149117 A1 | 7/2005 | Khosravi et al. |
| 2007/0231366 A1 | 10/2007 | Sawhney et al. |
| 2009/0011043 A1 | 1/2009 | Xie |
| 2013/0006300 A1 | 1/2013 | Michlitsch |
| 2014/0058442 A1 | 2/2014 | Tegels et al. |

FOREIGN PATENT DOCUMENTS

| | | |
|---|---|---|
| JP | 6181979 | 7/1994 |
| JP | H6-181979 | 7/1994 |
| WO | 97/41164 | 11/1997 |
| WO | 99/01195 | 1/1999 |
| WO | 99/47190 | 9/1999 |

OTHER PUBLICATIONS

Dintenfass, Effect of Velocity Gradient on the Clotting Time of Blood and on the Consistency of Clots Formed in Citro, Circulation Research, Apr. 1966, pp. 349-356, vol. XVIII, No. 4. Reference submitted in U.S. Appl. No. 14/756,544.

Thatcher, "Groin Bleeds and Other Hemorrhagic Complications of Cardiac Catheterization: A list of relevant issues," Cath Lab Digest, Mar. 2008, vol. 16, Issue 3. Reference submitted in U.S. Appl. No. 14/756,544.

Non-Final Office Action dated Jul. 6, 2017 in related U.S. Appl. No. 14/756,544.

(56) References Cited

OTHER PUBLICATIONS

Final Office Action dated Jan. 18, 2018 in related U.S. Appl. No. 14/756,544.
Non-Final Office Action dated May 14, 2018 in related U.S. Appl. No. 14/756,544.

* cited by examiner

FAILSAFE PERCUTANEOUS WOUND BARRIER

CROSS-REFERENCE TO RELATED APPLICATIONS

The present application is a Continuation Application of pending U.S. patent application Ser. No. 14/756,544, filed Sep. 16, 2015, which is a Continuation-In-Part Application of U.S. patent application Ser. No. 13/162,655, filed Jun. 17, 2011, claims priority under 35 USC § 119(e) to U.S. Provisional Patent Application 61/398,389, filed Jun. 24, 2010; U.S. Provisional Patent Application 61/404,358, filed Oct. 1, 2010; and U.S. Provisional Patent Application 61/404,935, filed Oct. 12, 2010, the entireties of which are incorporated herein by reference.

FIELD OF THE INVENTION

The invention generally relates to isolating a percutaneous vessel access region from its fluid communication with internal bleeding pathways.

BACKGROUND

Blood vessels are commonly used as a conduit to access internal patient anatomy for assessing medical needs and performing surgical procedures. Access through blood vessels allows surgical procedures to be performed while greatly reducing trauma and recovery time for the patient. Such procedures are generally regarded as minimally invasive procedures in contrast to open surgery procedures, the latter of which cut a patient open for access and create much larger wounds to be closed following a surgical procedure.

In 1953, Sven Seldinger developed a minimally invasive percutaneous access technique that is still commonly used today. This technique, known as Seldinger access, typically consists of several basic steps. A blood vessel, such as the femoral artery, is punctured through the skin surface using a hollow syringe needle. A guidewire is threaded through the needle into the artery, and the needle is removed by sliding it out over the guidewire. A cannula known as a dilator is inserted through a larger diameter tube known as a sheath, and both are advanced over the guidewire into the blood vessel, thus also assisting with later closure of the wound by having minimized disruption of the wounded tissue. The dilator and guidewire are removed from the sheath, leaving the sheath spanning from the outside of the patient to the inside of the blood vessel. The sheath provides an access port to the inside of the blood vessel through which large-diameter catheters and other surgical instrumentation may be advanced into, and traversed around, the patient's body. The sheath also serves to seal the wound from bleeding prior to completion of a further medical procedure through the wound. An anticoagulant such as heparin is typically administered to the patient so that the instrumentation placed into the blood vessel does not precipitate dangerous blood clots within the vasculature. Upon completion of the medical procedure, all instrumentation and the sheath are removed from the patient. The access wound site is typically subjected to manual compression until a clot has established to sufficiently stop bleeding from the vessel wound.

The use of manual compression for wound closure following a minimally invasive percutaneous surgical procedure is the "gold standard" by which all alternative methods of wound closure are evaluated for safety, reliability, and efficacy. However, wound closure by manual compression can be a slow process, particularly in the presence of anticoagulants. This led to a plethora of wound closure inventions that sought to expedite wound closure. Some, by example Khosravi et al. in US Application 2005/0149117 A1, followed Seldinger's efforts to seal or assist sealing of percutaneous wounds early in the process of performing a percutaneous medical access procedure. Khosravi did this by early deployment of a wound closure approach selected from a broad choice of agents, materials, or devices to seal or assist in sealing a percutaneous wound site. Most similar to the present invention, Nowakowski in U.S. patent application Ser. No. 13/162,655, also advocated early deployment of an agent for wound closure and did so in a manner like the present invention, but failed to fully specify a different and substantial further beneficial utility of the approach employed, as will now become clearer in the prophylactic subject matter of the present invention. Despite the above prior art and numerous other percutaneous wound closing inventions, acceptable success rates remains elusive in the clinic due largely to external reasons, e.g., inherent anatomical variability in patients, with the resultant persistent bleeding complications regarded as far outweighing the cardiovascular complications of the primary reason for a surgical procedure. This is summarized in an article authored by Jackson Thatcher, MD, FACC, Director of Inpatient Cardiology for the Park Nicollet Heart Center at Methodist Hospital St. Louis Park, for *Cath Lab Digest*, (March 2008) entitled "*Groin Bleeds and other Hemorrhagic Complications of Cardiac Catheterization: A list of relevant issues*" Volume 16 (Issue 3), retrieved from http://www.cathlabdigest.com/articles/Groin-Bleeds-and-Other-Hemorrhagic-Complications-Cardiac-Catheterization-A-list-relevant-is. The article lists percutaneous accessed arterial bleeds as the number one " . . . major cause of morbidity and mortality associated with cardiac catheterization procedures and percutaneous coronary interventions" with failed percutaneous wound closure technologies alone comprising only a very small portion of the root causes cited. In contrast, the present invention compensates for the vast majority of root causes cited in the article, not by offering yet another percutaneous wound closure technology, but by providing a barrier to protect a patient when a wound closure technology fails or is otherwise rendered ineffective in the presence of contributing factors.

SUMMARY OF THE INVENTION

The invention provides for various systems, methods, and devices to reduce or prevent percutaneous wound bleeding complications.

The invention provides for a failsafe barrier to internal bleeding pathways when a percutaneous wound closure fails to stop bleeding.

The invention may be used to direct vessel bleeding out a wound site access tract of the patient and away from other subcutaneous anatomical areas of a patient.

The invention may be used in combination with other wound closure systems, methods, and devices, to assist in or enhance closing a wound while also serving to substantially block internal bleeding pathways leading to complications.

The invention may be used to alter the anatomical structure of a percutaneous wound area through creation of substantial blood tissue capable of isolating internal bleeding pathways from the source of bleeding.

The invention may be supplied with an indicator to allow control of pressure buildup when filling a failsafe barrier mold cavity.

The invention may be combined with enhancements comprising management of anticoagulants, clot initiators, clot accelerants, pain killers, anti-lytic agents, and the like.

The invention may be supplied as a kit by itself or in combination with components used for any other procedure to be performed upon a patient.

The objects and advantages of the invention will appear more fully from the following detailed description of a preferred embodiment of the invention in conjunction with the accompanying drawings.

DETAILED DESCRIPTION OF THE PREFERRED EMBODIMENTS

One aspect of the approaches described herein comprises using familiar elements of a percutaneous medical procedure for new functions. These functions may also be described in the context of method steps, systems or system components, apparatus, or any combination thereof for teaching the invention or sorting as necessary for patent claims.

When referring to bleeding "complications" or "complication" and the like the general intent, unless expressly stated otherwise, is to refer to blood causing unacceptable blood accumulation and/or transfer beneath the skin such as in pseudoaneurysms, hematomas, retroperitoneal bleeding, and the like.

When referring to a "vessel" and absent any stipulation to the contrary, this generally refers to the vessel subject of the arteriotomy for vascular access.

The invention departs from a conventional way of looking at its elements. For example, the subcutaneous area comprising interstitial loose connective tissue, blood vessels, cutaneous tissue, muscle, and like anatomical features in the access site area may be referred to as a "mold" or the like with an introducer sheath or like instrument, when present, representing what may be referred to as a "core pin" extending into the mold. Clotting material, such as blood, injected to fill the mold subsequently solidifies to become what may be referred to as a mold "casting." The casting need not be removed from the mold, and typically both the casting and parts of the mold, like the tissue tract, would be reabsorbed or the like by the patient's body over time. Concerning vessel wound management in general, the invention is largely unconcerned with directly the vessel's wound puncture or its closure, and is more concerned with the surrounding anatomical space and any inserted instruments. The preferred intent here is to form a failsafe barrier substantially encasing the entire wound area and vessel to preventing bleeding from a failed wound closure, generally accomplished by preferably filling and clotting within internal anatomical spaces and fluid pathways that could otherwise give rise to bleeding complications when a wound closure fails. Users wanting to provide the patient such a failsafe barrier may also find benefits in a subsequently applied wound closure's performance comprising cost savings, improved ease of use, improved success rate, ability to use with larger French size instruments and vessel holes, or the like. As such, one embodiment of the present invention also specifically includes providing a failsafe barrier to internal bleeding pathways and enhanced performance of a wound closure approach used.

The clotting or clottable agent may be anything that converts from a material that can flow, into a material that is substantially stationary with liquids, gels, beads, and powders comprising four such examples. In the case of using blood, the clotted blood can also be considered to form a blood "tissue" when clotted. In such case, the invention can also be thought of as changing the patient's anatomy that is subject to a subsequent wound closure.

Performance enhancements that may be used with the present invention for initiating or accelerating clot formation, reducing lysis of formed clot, providing pain reduction, providing clotting agent radiopacity to observe placement, and the like are discussed in the reference documents and other publications. Likewise, the choice of clotting agents, sequence of deploying a clotting agent or agents, timing of deploying a clotting agent or agents, options for apparatus, methods, and systems employed to practice the invention can all be selected from the reference documents and other publications.

Figure 1:
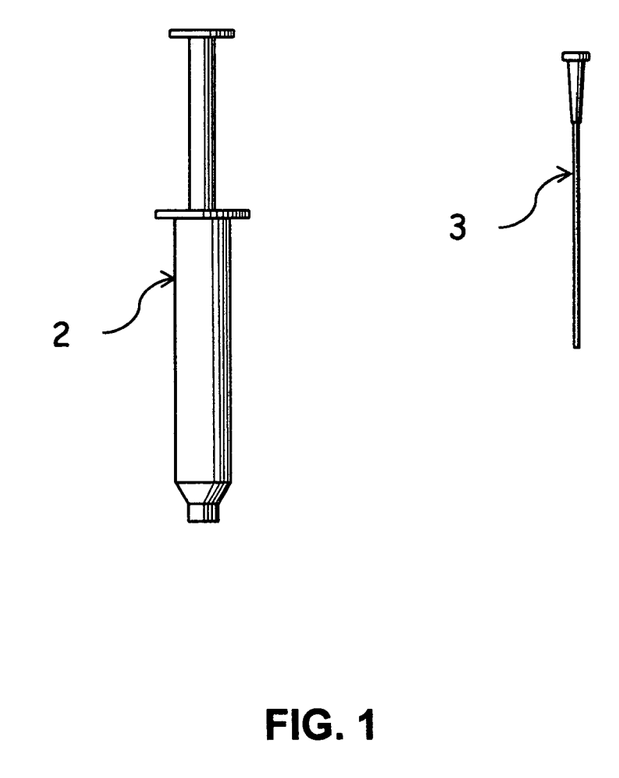
FIG. 1 depicts a side elevation view of a collection of exemplary elements for performing a version of the invention described herein, such as a sheath 1, a syringe 2 and a catheter 3.
Figure 2:
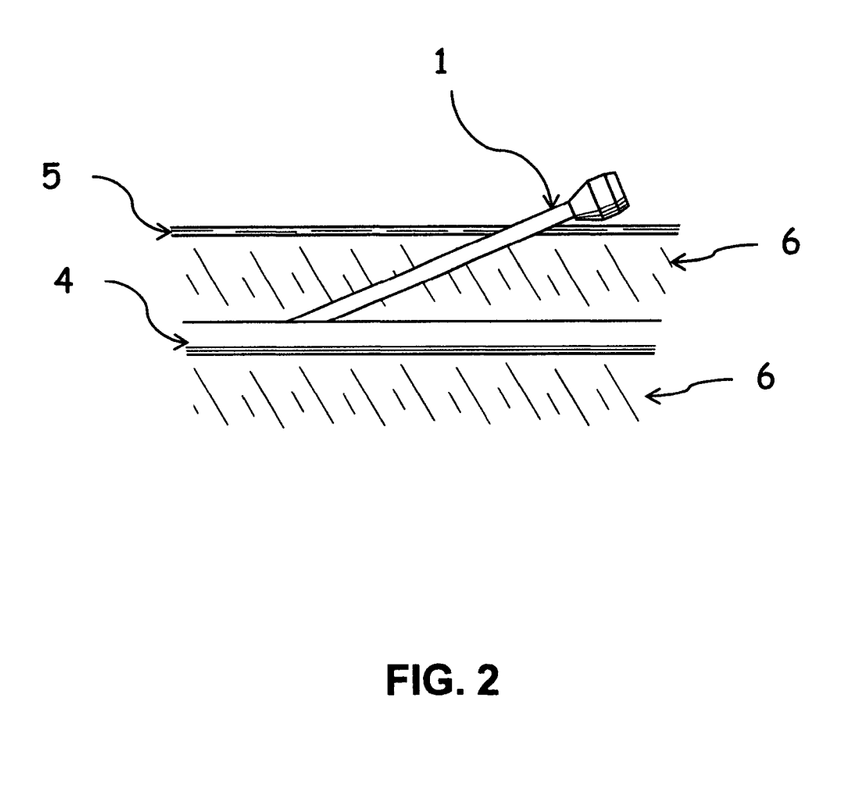
FIG. 2 depicts a side elevation partial cutaway view of elements involved in one step of an preferred approach as described herein, wherein the sheath 1 accesses a vessel 4 by extending into the vessel 4 through skin 5 and typically loose connective tissue 6 surrounding vessel 4, such as through the Seldinger technique.
Figure 3:
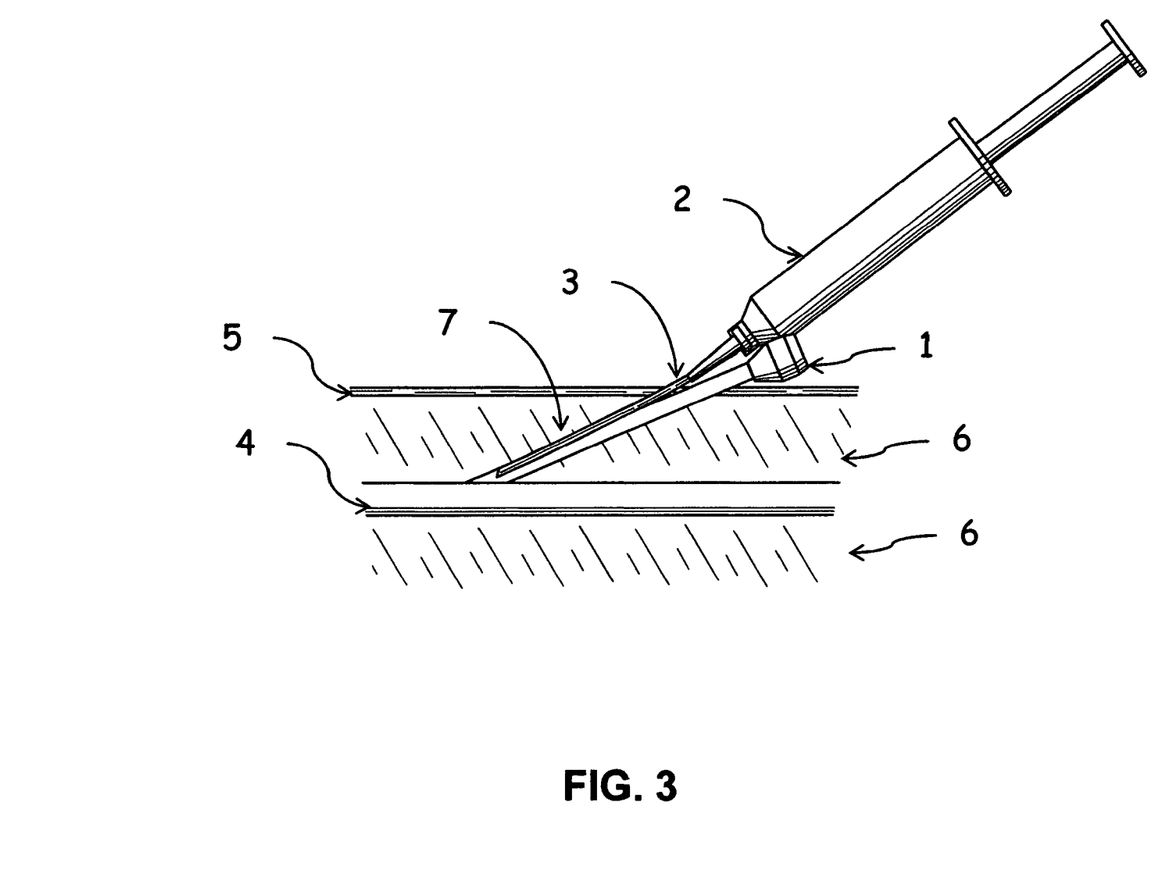
FIG. 3 depicts a side elevation partial cutaway view of elements involved in a further step of the preferred approach, wherein the catheter 3 is attached to the syringe 2 and advanced down a tissue tract 7 alongside the sheath 1 without advancing into the vessel 4.
Figure 4:
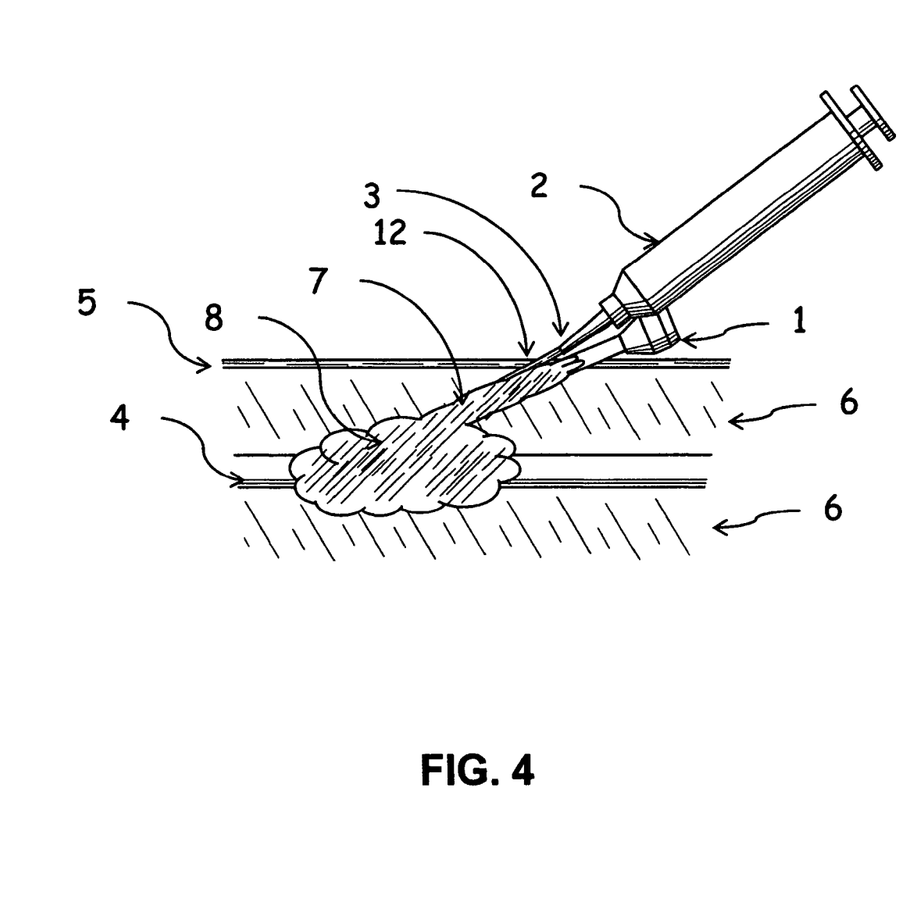
FIG. 4 depicts a side elevation partial cutaway view of elements involved in a further step of the preferred approach, wherein blood 8 is injected from the syringe 2 through the catheter 3 to around the vessel 4, vessel wound (now hidden) and along the tissue tract 7 around sheath 1 until blood 8 preferably emerges at skin 5 surface access site 12.
Figure 5:
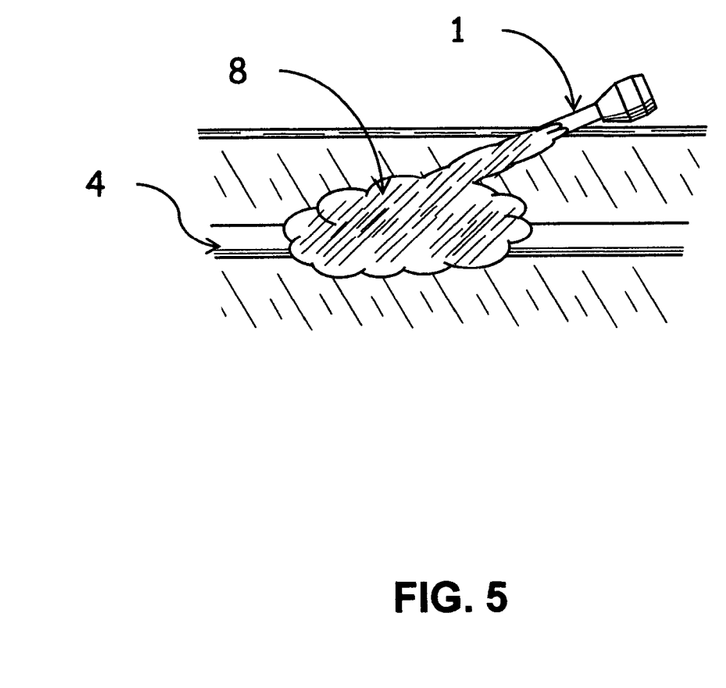
FIG. 5 depicts a side elevation partial cutaway view of elements involved in a further step of the preferred approach, wherein the syringe 2 and catheter 3 are removed from the patient while the blood 8 typically continues clotting, and the sheath 1 is available for intravascular medical procedures.
Figure 6:
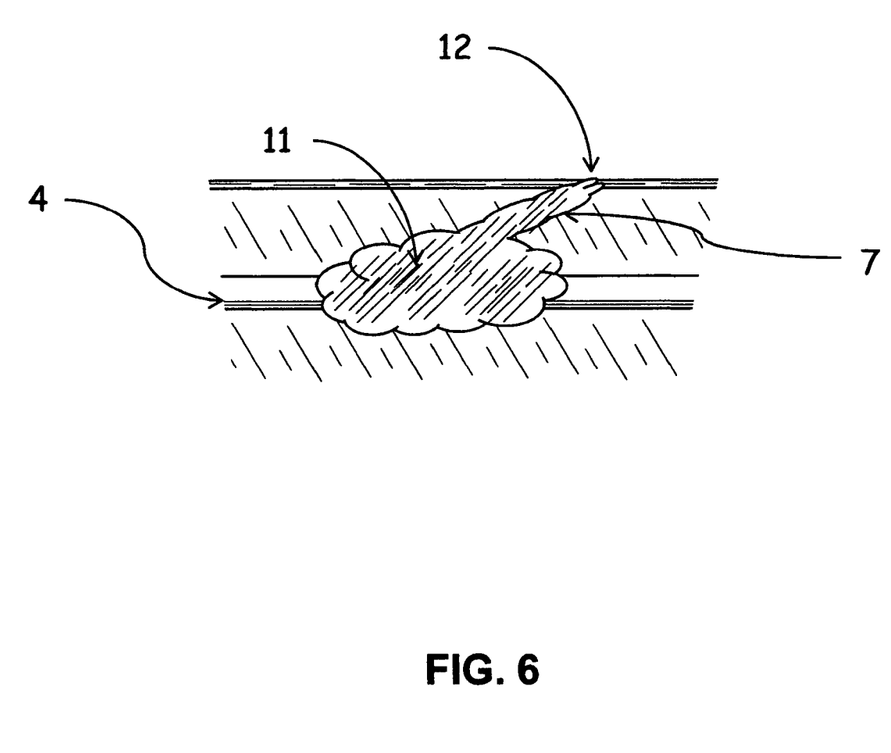
FIG. 6 depicts a side elevation partial cutaway view of preferred elements of the clotted failsafe barrier upon removal of instruments from the patient's wound site, comprising the typically clotted blood tissue casting 11 both encasing the vessel 4, its wound (not shown) and extending through the tissue tract 7 to the skin surface access site 12.

A preferred approach to practicing the invention begins with apparatus illustrated in FIG. 1 typically comprising a disposable syringe 2 and cannula 3, exemplifying both the potential very low cost and simplicity benefits associated with the invention. The cannula may comprise any instrument for providing fluid communication between a source of clottable agent and the mold cavity. In FIG. 2, an instrument such as an introducer sheath 1 is inserted through the skin 5, other tissue 6 generally surrounding the vessel 4, and into the vessel 4, as is typically done to establish a percutaneous access site for a medical procedure. The syringe 2 of FIG. 1 is typically filled with blood available through the sheath 1 from vessel 4 of FIG. 2. The blood-filled syringe 2 and cannula 3 of FIG. 1 are combined, and as shown in FIG. 3, then inserted through the skin 5 alongside the sheath 1 through tissue tract 7. Referring to FIG. 4, a sufficient volume of clottable blood 8 to create a failsafe barrier, is injected to fill the general wound site area thereby typically encasing both vessel 4 and sheath 1 as present in tissue tract 7 until injected blood typically flows out of the skin 5 access site 12. Absent an optional pressure gauge, the user can watch for unacceptable swelling at the skin surface, and if needed, also use the syringe to remove some of the injected blood to reduce pressure within the mold cavity and internal bleeding pathways when present through or around other tissue 6. In FIG. 5, the deposited blood advances its clot formation toward becoming a solid tissue mass while sheath 1 remains available for use in other intravascular medical procedures. In FIG. 6, the access sheath 1 (not shown) has been removed and the clotting blood has transformed into the substantially solid tissue mass casting 11. In cross section illustration of FIG. 7, details of the substantially solid tissue mass casting 11 are illustrated showing it substantially encasing vessel 4, vessel wound 10, and extending through the tissue tract 7 to the skin 5, and typically having a core pin channel impression 9 molded within as left behind by removed instrumentation (not shown) thus preferably directing any bleeding from wound 10 through channel 9 to out of the patient's skin 5 at access site 12. The tissue casting 11 also typically forms within available internal bleeding pathways (not shown) in and around surrounding tissue 6, vessel 4, skin 5, and any other anatomical features (not shown) in contact with the tissue casting. All these surfaces and any instruments present typically contribute to forming the mold for creating the tissue casting. As such, the form and size of blood tissue casting 11 providing the failsafe barrier to bleeding complications as illustrated in FIG. 7, will vary significantly by patient and procedure as it molds upon different surfaces present.

Figure 7:
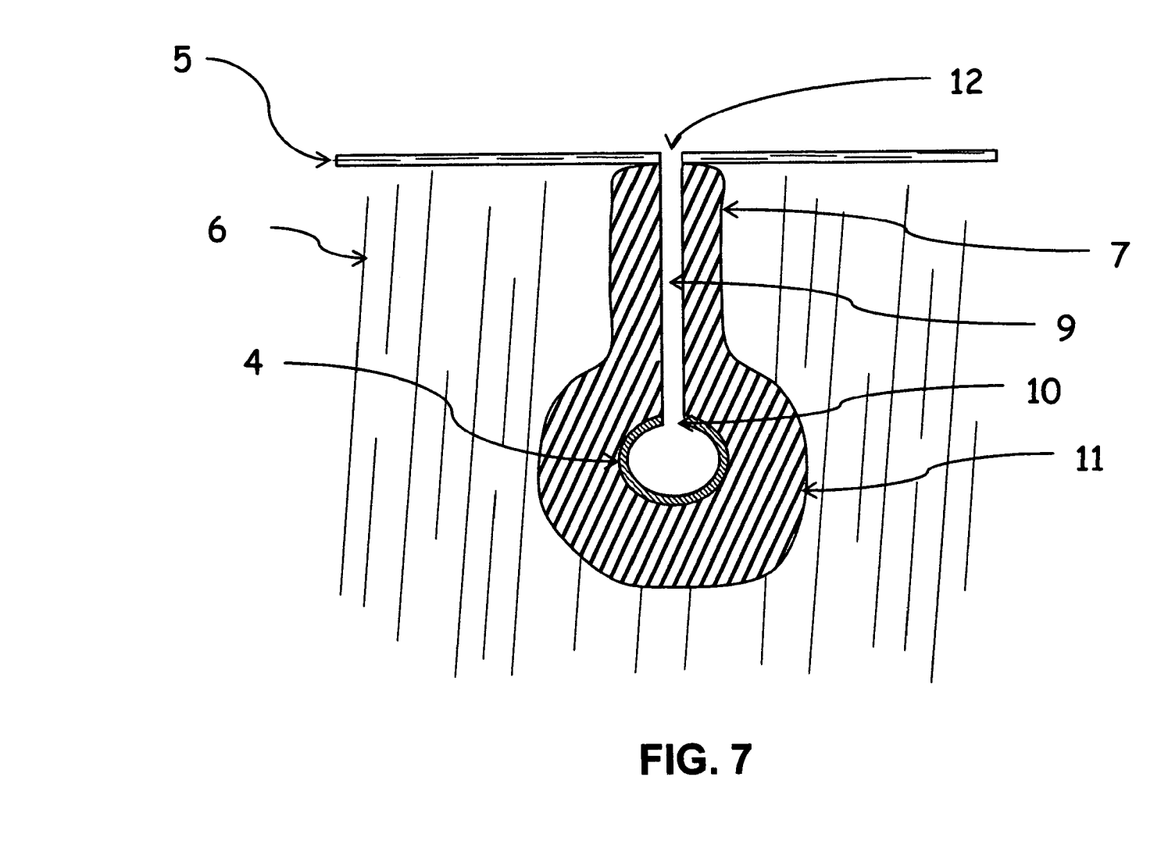
FIG. 7 depicts a radial elevation partial cutaway view of preferred elements of the clotted failsafe barrier upon removal of instruments from the patient's wound site, comprising the typically clotted blood tissue casting 11 substantially encasing the vessel 4 with its wound 10, and extending through the tissue tract 7 to the skin 5, and typically having an open channel impression 9 molded within the blood tissue casting 11 left behind by removed instrumentation (not shown) thus preferably directing any bleeding from wound 10 along channel 9, to out of the patient's skin 5 at access site 12 and substantially preventing internal bleeding pathways into areas of the typically surrounding tissue 6 and beyond (not shown.)

Further to FIG. 7, upon removal of a sheath or other percutaneously positioned instrument (not shown), the core pin casting cavity 9, typically may be used for further access to vessel 4 for further transcoronary procedural instruments, deploying a wound closure, or the like. In the case of using compression as the wound closure approach, the core pin casting cavity 9 may simply be collapsed during compression.

Some specialized tools may be useful in carrying out the invention in different ways, for example, injecting blood with syringe 2 versus ejecting blood from vessel 4 to deploy a failsafe barrier typically as described herein and in reference documents. Pulsatile indicators like described in reference documents and elsewhere, may optionally instead be used to indicate and, therefore allow controlled adjustment of, clotting agent pressure developing in the patient's wound site mold cavity when ensuring adequate placement to form a failsafe barrier. Radiopacity may be added to a clotting agent to enhance visualization of how well a clotting agent is deployed. Sheaths or a similar instrument, already know in the art to serve multiple useful purposes, can now also be used as a failsafe barrier mold core pin.

The present invention may also include kits comprising or consisting of any devices or combinations of devices described herein or though related references, and typically instructions for their use. Examples of devices suitable for kits may for example comprise a Seldinger needle, guidewire, a dilator, a sheath, a catheter, a cannula, a blood dispensing tool, a syringe, and pressure gauge. A comprehensive kit may preferably comprise components required to perform intravascular access such as through Seldinger technique, components useful in forming a failsafe barrier to bleeding, components useful in performing a wound closure, and instructions for use. A preferred reduced kit of the present invention may comprise a syringe, cannula attachable to the syringe, and instructions for use in forming a failsafe blood barrier. A preferred minimum kit may comprise instructions for using other medical hardware to create a failsafe barrier to bleeding. Having labels or having instructions for use may be separate or in any combination with a kit and typically provided by a manufacturer, a seller, or a distributor of any form of kit, and done so in any manner allowed by a governing agency, such as the United States Food and Drug Administration. Any and all kit examples above may be recombined, added to, or deleted from, as may be the preference.

All patents, patent publications, and peer-reviewed publications (i.e., "references") cited as part of the present patent application are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

What is claimed is:

1. A kit for use in forming a failsafe percutaneous wound barrier, the kit comprising:
   a clotting agent transfer apparatus; and
   instructions for forming the failsafe percutaneous wound barrier, the instructions comprising instructions directing a practitioner to
      deliver, by the clotting agent transfer apparatus, a tissue forming fluid to a subcutaneous region at least partially surrounding a vessel wound in a body of a patient,
      fill the subcutaneous region with the tissue forming fluid, and
      maintain a position of at least a portion of the apparatus within an access path through skin of the patient for a period of time to allow the tissue forming fluid to at least partially solidify into a tissue mass;
      wherein the tissue mass is capable of being reabsorbed by the body of the patient; and
      wherein, upon removing the apparatus from the access path, a core pin channel impression in the form of the portion of the apparatus is exposed via an opening in the skin of the patient, wherein the core pin channel impression provides a channel for directing any bleeding out to the skin of the patient, thereby providing a failsafe mechanism to avoid internal bleeding.

2. The kit of claim 1, wherein the instructions comprise instructions for forming the access path.

3. The kit of claim 1, wherein the apparatus comprises a cannula for providing fluid communication between a source of the tissue forming fluid and the subcutaneous region via the access path.

4. The kit of claim 3, wherein the apparatus comprises the source of the tissue forming fluid.

5. The kit of claim 4, wherein the source is a syringe.

6. The kit of claim 1, wherein the apparatus comprises a sheath.

7. The kit of claim 1, wherein the apparatus comprises a needle.

8. The kit of claim 1, wherein the apparatus comprises a dilator for minimizing disruption of wounded tissue along the access path.

9. The kit of claim 1, wherein the apparatus comprises an indicator for identifying fullness of the subcutaneous region.

10. The kit of claim 1, wherein the instructions further direct the practitioner to, while filling the subcutaneous region, monitor the fullness of the subcutaneous region.

11. The kit of claim 1, wherein the instructions further direct the practitioner to, after removing the apparatus, apply compression, thereby collapsing the core pin channel impression.

12. The kit of claim 1, wherein the instructions further inform the practitioner that, after removing the apparatus, the core impression channel is configured to accept introduction of another instrument for performing an additional medical procedure.

13. The kit of claim 1, wherein the tissue forming fluid comprises a clotting agent.

14. The kit of claim 13, comprising the clotting agent.

15. A kit for use in closing a percutaneous wound in a failsafe manner, the kit comprising:
  an apparatus for placing a clotting agent in internal bleeding pathways in a body of a patient while in a flowable form; and
  instructions for use, the instructions comprising instructions for performing a method comprising
   positioning, via an access path, a portion of the apparatus through skin of a patient,
   placing, using the apparatus, the clotting agent in the internal bleeding pathways at least partially surrounding a percutaneous vessel of the patient while in the flowable form,
   maintaining a position of the portion of the apparatus for a period of time to allow the clotting agent to at least partially solidify into a tissue cast formed within the internal bleeding pathways at least partially surrounding the percutaneous vessel;
   wherein the tissue cast, after solidification, is capable of being reabsorbed by the body of the patient over time, and comprises a core pin casting cavity in the form of the portion of the apparatus; and
   wherein, upon removal of the apparatus from the access path, the core pin casting cavity provides a channel for directing any bleeding out to the skin of the patient, thereby closing the percutaneous wound in the failsafe manner.

16. The kit of claim 15, wherein:
the clotting agent comprises autologous whole blood; and
the tissue cast is formed in part of the autologous whole blood.

17. The kit of claim 15, wherein the tissue cast is formed within a percutaneous region defined by one or more of interstitial loose connective tissue, blood vessels, cutaneous tissue, and muscle tissue.

18. The kit of claim 15, wherein the apparatus comprises a cannula.

19. The kit of claim 18, wherein the apparatus comprises a syringe attachable to the cannula.

20. The kit of claim 15, wherein the apparatus comprises a pressure gauge for gauging pressure of the clotting placement in the internal bleeding pathways during placement.

* * * * *